US006893470B1

(12) United States Patent
Lang et al.

(10) Patent No.: US 6,893,470 B1
(45) Date of Patent: May 17, 2005

(54) KERATINOUS FIBRE OXIDATION DYEING COMPOSITION CONTAINING A LACCASE AND DYEING METHOD USING SAME

(75) Inventors: Gérard Lang, Saint Prix (FR); Jean Cotteret, Verneuil sur Seine (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/600,128

(22) PCT Filed: Dec. 22, 1998

(86) PCT No.: PCT/FR98/02831

§ 371 (c)(1),
(2), (4) Date: Sep. 13, 2000

(87) PCT Pub. No.: WO99/36039

PCT Pub. Date: Jul. 22, 1999

(30) Foreign Application Priority Data

Jan. 13, 1998 (FR) .............................. 98 00258

(51) Int. Cl.$^7$ ................................. A61K 7/06
(52) U.S. Cl. ................. 8/401; 8/405; 8/408; 8/409; 8/423
(58) Field of Search .......................... 8/401, 405, 408, 8/423, 409, 410, 411

(56) References Cited

U.S. PATENT DOCUMENTS

| 3,061,432 A | 10/1962 | Menzel et al. ............... 430/376 |
| 3,227,554 A | 1/1966 | Barr et al. ....................... 96/55 |
| 3,251,742 A | 5/1966 | Soloway ......................... 8/401 |
| 3,419,391 A | 12/1968 | Young |
| 3,705,896 A | 12/1972 | Bailey ..................... 260/240 E |
| 3,725,067 A | 4/1973 | Bailey et al. ................. 96/56.5 |
| 3,926,631 A | 12/1975 | Arai et al. ...................... 96/29 |
| 4,003,699 A | 1/1977 | Rose et al. ..................... 8/409 |
| 4,128,425 A | 12/1978 | Greenwald ................. 430/440 |
| 4,500,630 A | 2/1985 | Sato et al. ................. 430/386 |
| 4,540,654 A | 9/1985 | Sato et al. .................. 430/381 |
| 4,621,046 A | 11/1986 | Sato et al. .................. 430/381 |
| 5,061,289 A | 10/1991 | Clausen et al. ................ 8/405 |
| 5,256,526 A | 10/1993 | Suzuki et al. ............... 430/384 |
| 5,380,340 A | 1/1995 | Neunhoeffer et al. .......... 8/409 |
| 5,430,159 A | 7/1995 | Neunhoeffer et al. ..... 548/371.4 |
| 5,441,863 A | 8/1995 | Tang et al. ................. 430/558 |
| 5,457,210 A | 10/1995 | Kim et al. ............... 548/262.4 |
| 5,534,267 A | 7/1996 | Neunhoeffer et al. ....... 424/701 |
| 5,769,902 A | 6/1998 | Samain .......................... 8/409 |
| 5,769,903 A | * | 6/1998 | Audousset et al. ............ 8/409 |
| 5,989,295 A | * | 11/1999 | de la Mettrie et al. ......... 8/406 |

FOREIGN PATENT DOCUMENTS

| WO | WO97/19998 | * 6/1997 |
| WO | WO 97/39727 | 10/1997 |

OTHER PUBLICATIONS

English language Derwent Abstract of JP 59–99437.
English language Derwent Abstract of JP 60–33552.
English language Derwent Abstract of JP 60–43659.
English language Derwent Abstract of JP 2–19576.
English language Derwent Abstract of JP 5–163124.
English language Derwent Abstract of JP 7–36159.
English language Derwent Abstract of JP 7–84348.
English language Derwent Abstract of JP 7–92632.
English language Derwent Abstract of JP 7–98489.
English language Derwent Abstract of JP 7–244361.

* cited by examiner

*Primary Examiner*—Mark Kopec
*Assistant Examiner*—Eisa Elhilo
(74) *Attorney, Agent, or Firm*—Finnegan, Henderson, Farabow, Garrett & Dunner LLP

(57) ABSTRACT

This invention concerns a ready-to-use composition for oxidation dyeing of keratinous fibres, and in particular human keratinous fibres such as hair comprising, in a suitable dyeing medium, at least a heterocyclic oxidation colouring agent, and at least an enzyme such as laccase, as well as the dyeing method using said composition.

37 Claims, No Drawings

KERATINOUS FIBRE OXIDATION DYEING COMPOSITION CONTAINING A LACCASE AND DYEING METHOD USING SAME The invention relates to a composition for the oxidation dyeing of keratin fibres, and in particular of human keratin fibres such as the hair, comprising, in a medium which is suitable for dyeing, at least one heterocyclic oxidation dye and at least one laccase-type enzyme, as well as to the dyeing process using this composition.

It is known practice to dye keratin fibres, and in particular human hair, with dye compositions containing one or more oxidation dye precursors, in particular ortho- or para-phenylenediamines, ortho- or para-aminophenols, and heterocyclic bases, which are generally known as oxidation bases. These oxidation dyes (oxidation bases) are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers allows a wide range of colours to be obtained.

The so-called "permanent" coloration obtained by means of these oxidation dyes should moreover satisfy a certain number of requirements. Thus, it should have no toxicological drawbacks, it should allow shades to be obtained in the desired intensity and it should have good staying power with respect to external agents (light, bad weather, washing, permanent-waving, perspiration or rubbing).

The dyes should also allow grey hair to be covered and, finally, they should be as unselective as possible, i.e. they should allow only the smallest possible differences in coloration to be obtained along the same keratin fibre, which may indeed be differently sensitized (i.e. damaged) between its tip and its root.

The oxidation dyeing of keratin fibres is generally carried out in alkaline medium, in the presence of hydrogen peroxide. However, the use of alkaline media in the presence of hydrogen peroxide can have the drawback of resulting in substantial degradation of the fibres, as well as a decolorization of the keratin fibres, which is not always desirable.

The oxidation dyeing of keratin fibres can also be carried out using oxidizing systems other than hydrogen peroxide, such as enzymatic systems. Thus, it has already been proposed in U.S. Pat. No. 3,251,742 and patent applications FR-A-2 112 549, FR-A-2 694 018, EP-A-0 504 005, WO 95/07988, WO 95/33836, WO 95/33837, WO 96/00290, WO 97/19998 and WO 97/19999, to dye keratin fibres with compositions comprising at least one oxidation dye, or at least one melanin precursor, in combination with laccase-type enzymes, the said compositions being placed in contact with atmospheric oxygen. Although these dye formulations are used under conditions which do not result in the degradation of keratin fibres comparable to that generated by dyes used in the presence of hydrogen peroxide, they lead to colorations that are still insufficient both in terms of the homogeneity of the colour distributed along the fibre (unison) and in terms of the chromaticity (luminosity) and dyeing power.

The Applicant has now discovered that it is possible to obtain novel dyes that are capable of giving more intense colorations without generating any significant degradation of keratin fibres, and that are relatively unselective and stand up well to the various attacking factors to which the fibres may be subjected, by combining at least one suitably selected heterocyclic oxidation dye (oxidation base and/or coupler) and at least one laccase-type enzyme.

This discovery forms the basis of the present invention.

A first subject of the invention is thus a ready-to-use composition for the oxidation dyeing of keratin fibres, and in particular of human keratin fibres such as the hair, characterized in that it comprises, in a medium which is suitable for dyeing, at least one oxidation dye chosen from heterocyclic oxidation bases and heterocyclic couplers, and at least one laccase-type enzyme, the said composition being free of heterocyclic coupler chosen from indole, indoline, monocyclic pyridine and phenazine compounds and free of heterocyclic oxidation base chosen from 4,5-diamino-6-hydroxypyrimidine and 3,4-diaminohydroxypyrazole.

The ready-to-use dye composition in accordance with the invention leads to intense, chromatic colorations. The colorations obtained with the ready-to-use dye composition in accordance with the invention moreover show little selectivity and excellent properties of resistance both with respect to atmospheric agents such as light and bad weather and with respect to perspiration and the various treatments to which hair may be subjected (washing, permanent-waving).

A subject of the invention is also a process for the oxidation dyeing of keratin fibres using this ready-to-use dye composition.

The laccase(s) used in the ready-to-use dye composition in accordance with the invention can be chosen in particular from laccases of plant origin, of animal origin, of fungal origin (yeasts, moulds or fungi) or of bacterial origin, it being possible for the organisms of origin to be monocellular or multicellular. The laccase(s) used in the ready-to-use dye composition in accordance with the invention can also be obtained by biotechnology.

Among the laccases of plant origin which can be used according to the invention, mention may be made of the laccases produced by plants which carry out chlorophyll synthesis, such as those mentioned in patent application FR-A-2 694 018.

Mention may be made in particular of the laccases present in extracts of *Anacardiacea* plants such as, for example, extracts of *Magnifera indica*, of *Schinus molle* or of *Pleiogynium timoriense*; in extracts of *Podocarpacea* plants, of *Rosmarinus* off., of *Solanum tuberosum*, of *Iris* sp., of *Coffea* sp., of *Daucus carrota*, of *Vinca minor*, of *Persea americana*, of *Catharanthus roseus*, of *Musa* sp., of *Malus pumila*, of *Gingko biloba*, of *Monotropa hypopithys* (Indian pipe), of *Aesculus* sp., of *Acer pseudoplatanus*, of *Prunus persica* and of *Pistacia palaestina*.

Among the laccases of fungal origin, optionally obtained by biotechnology, which can be used according to the invention, mention may be made of the laccase(s) obtained from *Polyporus versicolor*, from *Rhizoctonia praticola* and from *Rhus vernicifera* as described, for example, in patent applications FR-A-2 112 549 and EP-A-504 005; the laccases described in patent applications WO 95/07988, WO 95/33836, WO 95/33837, WO 96/00290, WO 97/19998 and WO 97/19999, the content of which forms an integral part of the present description, such as, for example, the laccase (s) obtained from *Scytalidium*, from *Polyporus pinsitus*, from *Myceliophthora thermophila*, from *Rhizoctonia solani*, from *Pyricularia oryzae*, and variants thereof. Mention may also be made of the laccase(s) obtained from *Trametes* versicolor, from *Fomes fomentarius*, from *Chaetomium thermophile*, from *Neurospora crassa*, from *Colorius versicolor*, from *Botrytis cinerea*, from *Rigidoporus lignosus*, from *Phellinus noxius*, from *Pleurotus ostreatus*, from *Aspergillus nidulans*, from *Podospora anserina*, from *Agaricus bisporus*, from *Ganoderma lucidum*, from *Glomerella cingulata*, from *Lactarius piperatus*, from *Russula delica*, from *Heterobasidion annosum*, from *Thelephora terrestris*, from *Cladosporium cladosporioides*, from *Cerrena unicolor*, from *Coriolus hirsutus*, from *Ceriporiopsis subvermispora*, from *Coprinus cinereus*, from *Panaeolus papilionaceus*, from *Panaeolus sphinctrinus*, from *Schizophyllum commune*, from *Dichomitius squalens*, and from variants thereof.

Laccases of fungal origin, optionally obtained by biotechnology, will more preferably be chosen.

The enzymatic activity of the laccases used in accordance with the invention and having syringaldazine among their substrates can be defined by the oxidation of syringaldazine under aerobic conditions. One Lacu unit corresponds to the amount of enzyme which catalyses the conversion of 1 mmol of syringaldazine per minute at a pH of 5.5 and at a temperature of 30° C. One U unit corresponds to the amount of enzyme which produces an absorbance delta of 0.001 per minute at a wavelength of 530 nm, using syringaldazine as substrate, at 30° C. and at a pH of 6.5. The enzymatic activity of the laccases used according to the invention can also be defined by the oxidation of para-phenylenediamine. One ulac unit corresponds to the amount of enzyme which produces an absorbance delta of 0.001 per minute at a wavelength of 496.5 nm, using para-phenylenediamine as substrate (64 mM), at 30° C. and at a pH of 5.

According to the invention, the enzymatic activity is preferably determined in ulac units.

Among the heterocyclic oxidation bases which can be used in the ready-to-use dye composition according to the invention, mention may be made in particular of pyrimidine derivatives and pyrazole derivatives, and the addition salts thereof with an acid.

Among the pyrimidine derivatives which may be mentioned more particularly are the compounds described, for example, in German patent DE 2 359 399 or Japanese patents JP 88-169 571 and JP 91-333 495, such as 2,4,5,6-tetraminopyrimidine, 4-hydroxy-2,5,6-triaminopyrimidine, and the addition salts thereof with an acid and pyrazolopyrimidine derivatives such as pyrazolo[1,5-a]pyrimidine-3,7-diamine, 2-methylpyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-amino-5-methylpyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 3-amino-7-β-hydroxyethylamino-5-methylpyrazolo-[1,5-a]pyrimidine, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-amino-pyrazolo[1,5-a]pyrimidin-3-yl)-(2-hydroxyethyl)amino]-ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo-[1,5-a]pyrimidine-3,7-diamine, and the addition salts thereof and the tautomeric forms thereof, when a tautomeric equilibrium exists.

Among the pyrazole derivatives which may be mentioned more particularly are the compounds described in patents or patent applications DE 3 843 892, DE 4 133 957, DE 4 234 886, WO 94/08969, WO 94/08970, DE 4 234 887, FR 2 733 749, FR 2 735 685, such as 4,5-diaminopyrazole, 4,5-diamino-1-methylpyrazole, 1-benzyl-4,5-diaminopyrazole, 3,4-diaminopyrazole, 1-benzyl-4,5-diamino-3-methylpyrazole, 4-amino-1,3-dimethyl-5-hydrazinopyrazole, 4,5-diamino-3-methyl-1-phenylpyrazole, 4,5-diamino-1-tert-butyl-3-methylpyrazole, 4,5-diamino-3-tert-butyl-1-methyl-pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole and 4,5-diamino-3-methyl-1-isopropylpyrazole, and the addition salts thereof with antacid.

Among the heterocyclic couplers which can be used in the ready-to-use dye composition in accordance with the invention, mention may be made in particular of benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo-[3,2-d]oxazoline derivatives, pyrazolo[3,4-d]thiazole derivatives, thiazoloazole S-oxide derivatives and thiazoloazole S,S-dioxide derivatives, and the addition salts thereof with an acid.

Among the benzimidazole derivatives which can be used as heterocyclic couplers in the dye composition in accordance with the invention, mention may be made more particularly of the compounds of formula (I) below, and the addition salts thereof with an acid:

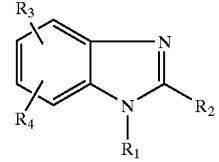

(I)

in which:

$R_1$ represents a hydrogen atom or a $C_1-C_4$ alkyl radical, $R_2$ represents a hydrogen atom or a $C_1-C_4$ alkyl or phenyl radical, $R_3$ represents a hydroxyl, amino or methoxy radical, $R_4$ represents a hydrogen atom or a hydroxyl, methoxy or $C_1-C_4$ alkyl radical;

with the proviso that:

when $R_3$ denotes an amino radical, then it occupies position 4, when $R_3$ occupies position 4, then $R_4$ occupies position 7, when $R_3$ occupies position 5, then $R_4$ occupies position 6.

Among the benzimidazole derivatives of formula (I) above which may be mentioned more particularly are 4-hydroxybenzimidazole, 4-aminobenzimidazole, 4-hydroxy-7-methylbenzimidazole, 4-hydroxy-2-methylbenzimidazole, 1-butyl-4-hydroxy-benzimidazole, 4-amino-2-methylbenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole and 5,6-dimethoxybenzimidazole, and the addition salts thereof with an acid.

Among the benzomorpholine derivatives which can be used as heterocyclic couplers in the ready-to-use dye composition in accordance with the invention, mention may be made more particularly of the compounds of formula (II) below, and the addition salts thereof with an acid:

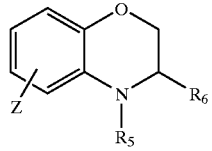

(II)

in which:

$R_5$ and $R_6$, which may be identical or different, represent a hydrogen atom or a $C_1-C_4$ alkyl radical, Z represents a hydroxyl or amino radical.

Among the benzomorpholine derivatives of formula (II) above which may be mentioned more particularly are 6-hydroxy-1,4-benzomorpholine, N-methyl-6-hydroxy-1,4-benzomorpholine and 6-amino-1,4-benzomorpholine, and the addition salts thereof with an acid.

Among the sesamol derivatives which can be used as heterocyclic couplers in the ready-to-use dye composition, mention may be made more particularly of the compounds of formula (III) below, and the addition salts thereof with an acid:

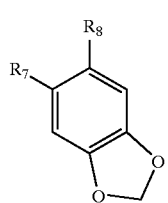

(III)

in which:

$R_7$ denotes a hydroxyl, amino, $(C_1-C_4)$alkylamino, monohydroxy$(C_1-C_4)$alkylamino or polyhydroxy $(C_2-C_4)$alkyl-amino radical, $R_8$ denotes a hydrogen or halogen atom or a $C_1-C_4$ alkoxy radical.

Among the sesamol derivatives of formula (III) above which may be mentioned more particularly are 2-bromo-4,5-methylenedioxyphenol, 2-methoxy-4,5-methylenedioxyaniline and 2-(β-hydroxyethyl)amino-4,5-methylenedioxybenzene, and the addition salts thereof with an acid.

Among the pyrazoloazole derivatives which can be used as heterocyclic couplers in the ready-to-use dye composition in accordance with the invention, mention may be made more particularly of the compounds described in the following patents and patent applications: FR 2 075 583, EP-A-119 860, EP-A-285 274, EP-A-244 160, EP-A-578 248, GB 1 458 377, U.S. Pat. No. 3,227,554, U.S. Pat. No. 3,419,391, U.S. Pat. No. 3,061,432, U.S. Pat. No. 4,500,630, U.S. Pat. No. 3,725,067, U.S. Pat. No. 3,926,631, UA 5 457 210, JP 84/99437, JP 83/42045, JP 84/162548, JP 84/171956, JP 85/33552, JP 85/43659, JP 85/172982, JP 85/190779 as well as in the following publications: Chem. Ber. 32, 797 (1899), Chem. Ber. 89, 2550, (1956), J. Chem. Soc. Perkin trans 1, 2047, (1977), J. Prakt. Chem., 320, 533, (1978); the teachings of which form an integral part of the present patent application.

Pyrazoloazole derivatives which may be mentioned most particularly are:
2-methylpyrazolo[1,5-b]-1,2,4-triazole,
2-ethylpyrazolo[1,5-b]-1,2,4-triazole,
2-isopropylpyrazolo[1,5-b]-1,2,4-triazole,
2-phenylpyrazolo[1,5-b]-1,2,4-triazole,
2,6-dimethylpyrazolo[1,5-b]-1,2,4-triazole,
7-chloro-2,6-dimethylpyrazolo[1,5-b]-1,2,4-triazole,
3,6-dimethylpyrazolo[3,2-c]-1,2,4-triazole,
6-phenyl-3-methylthiopyrazolo[3,2-c]-1,2,4-triazole,
6-aminopyrazolo[1,5-a]benzimidazole,
and the addition salts thereof with an acid.

Among the pyrroloazole derivatives which can be used as heterocyclic couplers in the ready-to-use dye composition in accordance with the invention, mention may be made more particularly of the compounds described in the following patent applications and patents: U.S. Pat. No. 5,256,526, EP-A-557 851, EP-A-578 248, EP-A-518 238, EP-A-456 226, EP-A-488 909, EP-A-488 248, and in the following publications:

D. R. Liljegren Ber. 1964, 3436;
E. J. Browne, J.C.S., 1962, 5149;
P. Magnus, J.A.C.S., 1990, 112, 2465;
P. Magnus, J.A.C.S., 1987, 109, 2711;
Angew. Chem. 1960, 72, 956;
and Rec. Trav. Chim. 1961, 80, 1075; the teachings of which form an integral part of the present patent application.

Pyrroloazole derivatives which may be mentioned most particularly are:
5-cyano-4-ethoxycarbonyl-8-methylpyrrolo[1,2-b]-1,2,4-triazole,
5-cyano-8-methyl-4-phenylpyrrolo[1,2-b]-1,2,4-triazole,
7-amido-6-ethoxycarbonylpyrrolo[1,2-a]benzimidazole,
and the addition salts thereof with an acid.

Among the imidazoloazole derivatives which can be used as heterocyclic couplers in the ready-to-use dye composition in accordance with the invention, mention may be made more particularly of the compounds described in the following patent applications and patents: U.S. Pat. No. 5,441,863; JP 62-279 337; JP 06-236 011 and JP 07-092 632, the teachings of which form an integral part of the present patent application.

Imidazoloazole derivatives which may be mentioned most particularly are:
7,8-dicyanoimidazolo[3,2-a]imidazole,
7,8-dicyano-4-methylimidazolo[3,2-a]imidazole, and the addition salts thereof with an acid.

Among the pyrazolopyrimidine derivatives which can be used as heterocyclic couplers in the ready-to-use dye composition in accordance with the invention, mention may be made more particularly of the compounds described in the following patent application: EP-A-304 001, the teaching of which forms an integral part of the present patent application.

Pyrazolopyrimidine derivatives which may be mentioned most particularly are:
pyrazolo[1,5-a]pyrimidin-7-one,
2,5-dimethylpyrazolo[1,5-a]pyrimidin-7-one,
2-methyl-6-ethoxycarbonylpyrazolo[1,5-a]pyrimidin-7-one,
2-methyl-5-methoxymethylpyrazolo[1,5-a]pyrimidin-7-one,
2-tert-butyl-5-trifluoromethylpyrazolo[1,5-a]pyrimidin-7-one,
2,7-dimethylpyrazolo[1,5-a]pyrimidin-5-one, and the addition salts thereof with an acid.

Among the pyrazoline-3,5-dione derivatives which can be used as heterocyclic couplers in the ready-to-use dye composition in accordance with the invention, mention may be made more particularly of the compounds described in the following patent applications and patents: JP 07-036159, JP 07-084348 and U.S. Pat. No. 4,128,425, and in the following publications:

L. WYZGOWSKA, Acta. Pol. Pharm. 1982, 39 (1–3), 83.

E. HANNIG, Pharmazie, 1980, 35 (4), 231

M. H. ELNAGDI, Bull. Chem. Soc. Jap., 46 (6), 1830, 1973

G. CARDILLO, Gazz. Chim. Ital. 1966, 96, (8–9), 973, the teachings of which form an integral part of the present patent application.

Pyrazoline-3,5-dione derivatives which may be mentioned most particularly are:

1,2-diphenylpyrazoline-3,5-dione, 1,2-diethylpyrazoline-3,5-dione, and the addition salts thereof with an acid.

Among the pyrrolo[3,2-d]oxazole derivatives which can be used as heterocyclic couplers in the ready-to-use dye composition in accordance with the invention, mention may be made more particularly of the compounds described in patent application JP 07 325 375, the teaching of which forms an integral part of the present patent application.

Among the pyrazolo[3,4-d]thiazole derivatives which can be used as heterocyclic couplers in the ready-to-use dye composition in accordance with the invention, mention may be made more particularly of compounds described in patent application JP 07 244 361 and in J. Heterocycl. Chem. 16, 13, (1979).

Among the thiazoloazole S-oxide and thiazoloazole S,S-dioxide derivatives which can be used as heterocyclic couplers in the ready-to-use dye composition in accordance with the invention, mention may be made more particularly of the compounds described in the following documents:

JP 07 09 84 89;

Khim. Geterotsilk. Soedin, 1967, p. 93;

J. Prakt. Chem., 318, 1976, p. 12;

Indian J. Heterocycl. Chem. 1995, 5 (2), p. 135;

Acta. Pol. Pharm. 1995, 52 (5), 415;

Heterocycl. Commun. 1995, 1 (4), 297;

Arch. Pharm. (Weinheim, Ger.), 1994, 327 (12), 825.

The heterocyclic oxidation dye(s), i.e. the heterocyclic oxidation base(s) and/or the heterocyclic coupler(s) preferably represents from 0.0001% to 12% by weight approximately relative to the total weight of the ready-to-use dye composition, and even more preferably from 0.005% to 6% by weight approximately relative to this weight.

The ready-to-use dye composition in accordance with the invention can also contain, in addition to the heterocyclic oxidation dyes defined above, at least one benzenic oxidation base and/or at least one benzenic coupler and/or at least one direct dye, in particular to modify the shades or to enrich them with glints.

Among the benzenic oxidation bases which may be additionally present in the ready-to-use dye composition in accordance with the invention, mention may be made in particular of para-phenylenediamines, bis(phenyl) alkylenediamines, ortho-phenylenediamines, para-aminophenols and ortho-aminophenols, and the addition salts thereof with an acid.

When they are used, these benzenic oxidation bases preferably represent from 0.0005% to 12% by weight approximately relative to the total weight of the dye composition, and even more preferably from 0.005% to 6% by weight approximately relative to this weight.

Among the benzenic couplers which may be additionally present in the ready-to-use dye composition in accordance with the invention, mention may be made in particular of meta-phenylenediamines, meta-aminophenols and meta-diphenols, and the addition salts thereof with an acid.

When they are present, these benzenic couplers preferably represent from 0.0001% to 10% by weight approximately relative to the total weight of the ready-to-use dye composition, and even more preferably from 0.005% to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates; lactates and acetates.

The medium which is suitable for dyeing (or support) for the ready-to-use dye composition in accordance with the invention generally consists of water or of a mixture of water and at least one organic solvent to dissolve the compounds which would not be sufficiently water-soluble.

The pH of the ready-to-use composition in accordance with the invention is chosen such that the enzymatic activity of the laccase is sufficient. It is generally between 4 and 11 approximately, and preferably between 6 and 9 approximately. It can be adjusted to the desired value by means of acidifying or basifying agents usually used in the dyeing of keratin fibres.

The ready-to-use dye composition in accordance with the invention can also contain various adjuvants conventionally used in compositions for dyeing the hair, such as anionic, cationic, nonionic, amphoteric or zwitterionic surfactants or mixtures thereof, polymers, antioxidants, enzymes other than the laccases used in accordance with the invention, such as, for example, peroxidases or 2-electron-oxidoreductases, penetrating agents, sequestering agents, fragrances, buffers, dispersants, film-forming agents, preserving agents, opacifiers, thickeners and vitamins.

Needless to say, the person skilled in the art will take care to select this or these optionally additional compound(s) such that the advantageous properties intrinsically associated with the ready-to-use dye composition in accordance with the invention are not, or are not substantially, adversely affected by the addition(s) envisaged.

The ready-to-use dye composition in accordance with the invention can be in various forms, such as in the form of liquids, creams or gels, which may be pressurized, or in any other form which is suitable for dyeing keratin fibres, and in particular human hair. In this case, the heterocyclic oxidation dye(s) and optionally the additional oxidation dye(s) and the laccase-type enzyme(s) are present in the same ready-to-use composition, and consequently the said composition should be free of gaseous oxygen, so as to avoid any premature oxidation of the oxidation dye(s).

A subject of the invention is also a process for dyeing keratin fibres, and in particular human keratin fibres such as the hair, using the ready-to-use dye composition as defined above.

According to this process, at least one ready-to-use dye composition as defined above is applied to the fibres for a period which is sufficient to develop the desired coloration, after which the fibres are rinsed, optionally washed with shampoo, rinsed again and dried.

The time required to develop the coloration on the keratin fibres is generally between 3 minutes and 60 minutes and even more specifically between 5 minutes and 40 minutes.

According to one specific embodiment of the invention, the process includes a preliminary step consisting in separately storing, on the one hand, a composition (A) comprising, in a medium which is suitable for dyeing, at least one oxidation dye chosen from the heterocyclic oxidation bases and heterocyclic couplers as defined above, and, on the other hand, a composition (B) comprising, in a medium which is suitable for dyeing, at least one laccase-type enzyme, and then in mixing them together at the time of use, after which this mixture is applied to the keratin fibres.

Another subject of the invention is a multi-compartment dyeing device or "kit" or any other multi-compartment packaging system, a first compartment of which contains composition (A) as defined above and a second compartment of which contains composition (B) as defined above. These devices may be equipped with a means for applying the desired mixture to the hair, such as the devices described in patent FR-2 586 913 in the name of the Applicant.

The example which follows is intended to illustrate the invention without thereby limiting its scope.

DYEING EXAMPLE

The following ready-to-use dye compositions were prepared (contents in grams):

| COMPOSITION | 1 | 2 |
| --- | --- | --- |
| 2,4,5,6-Tetraaminopyrimidine sulphate (heterocyclic oxidation base) | 0.65 | — |
| para-Phenylenediamine (benzenic oxidation base) | — | 0.20 |
| Resorcinol (benzenic coupler) | 0.30 | — |
| 2-Methoxy-4,5-methylenedioxyaniline monohydrochloride (heterocyclic coupler) | — | 0.37 |
| Laccase obtained from Rhus vernicifera at 180 units/mg, sold by the company Sigma | 1.8 | 1.8 |
| Common dye support (*) | (*) | (*) |
| Demineralized water qs | 100 g | 100 g |

(*): Common dye support:
Ethanol 20.0 g
(C8–C10)alkylpolyglucoside as an aqueous solution containing 60% active material (A.M.), sold under the name Oramix CG110 ® by the company Seppic 4.8 g A.M.
Agent for pH q.s. pH = 6.5

Each of the ready-to-use dye compositions described above was applied to locks of natural grey hair containing 90% white hairs, for 40 minutes at a temperature of 30° C. The hair was then rinsed, washed with a standard shampoo and then dried.

The hair was dyed in the shades given in the Table below:

| EXAMPLE | Shade obtained |
| --- | --- |
| 1 | Coppery mahogany light blond |
| 2 | light blond |

In the dye compositions described above, the laccase from *Rhus vernicifera* at 180 units/mg, sold by the company Sigma, can be replaced with 1.0 g of laccase from *Pyricularia oryzae* at 100 units/mg, sold by the company ICN.

What is claimed is:

1. A composition for the oxidation dyeing of keratin fibers, comprising:
   (a) at least one oxidation dye chosen from heterocyclic oxidation bases, heterocyclic couplers, and acid addition salts of said oxidation dyes; and
   (b) at least one laccase-type enzyme,
      provided that said composition does not comprise a heterocyclic oxidation base chosen from 4,5-diamino-6-hydroxy-pyrimidine and 3,4-diaminohydroxy-pyrazole, and
      provided that said composition does not comprise a heterocyclic coupler chosen from indole, indoline, monocyclic pyridine, and phenazine compounds.

2. The composition according to claim 1, wherein said keratin fibers are human keratin fibers.

3. The composition according to claim 2, wherein said human keratin fibers are hair.

4. The composition according to claim 1, wherein said at least one enzyme of the laccase type is chosen from laccases of plant origin, laccases of animal origin, laccases of fungal origin, and laccases of bacterial origin; and laccases obtained by biotechnology.

5. The composition according to claim 1, wherein said at least one enzyme of the laccase type is of plant origin and is chosen from the laccases extracted from plants chosen from *Anacardiaceae, Podocarpaceae, Rosmarinus* off., *Solanum tuberosum, Iris* sp., *Coffea* sp., *Daucus carrota, Vinca minor, Persea americana, Catharenthus roseus, Musa* sp., *Malus pumila, Gingko biloba, Monotropa hypopithys, Aesculus* sp., *Acer pseudoplatanus, Prunus persica,* and *Pistacia palaestina.*

6. The composition according to claim 1, wherein said at least one enzyme of the laccase type is chosen from the laccases obtained from fungi chosen from *Polyporus versicolor, Rhizoctonia praticola, Rhus vernicifera, Scytalidium, Polyporus pinsitus, Myceliophtora thermophila, Rhizoctonia solani, Pyricularia orizae, Tramates versicolor, Fomes fomentarius, Chaetomium thermophile, Neurospora crassa, Colorius versicol, Botrytis cinerea, Rigidoporus lignosus, Phellinus noxius, Pleurotus ostreatus, Aspergillus nidulans, Podospora anserina, Agaricus bisporus, Ganoderma lucidum, Glomerella cingulata, Lactarius piperatus, Russula delica, Heterobasidion annosum, Thelephora terrestris, Cladosporium cladosporioides, Cerrena unicolor, Coriolus hirsutus, Ceriporiopsis subvermispora, Coprinus cinereus, Panaeolus papilionaceus, Panaeolus sphinctrinus, Schizophyllum commune, Dichomitius squalens,* and variants of all said fungi.

7. The composition according to claim 1, wherein said at least one enzyme of the laccase type is in an amount ranging from 0.5 Lacu to 200 Lacu units per 100 g of said composition.

8. The composition according to claim 1, wherein said heterocyclic oxidation bases are chosen from pyrimidine derivatives, pyrazole derivatives, and acid addition salts of said heterocyclic oxidation bases.

9. The composition according to claim 8, wherein said pyrimidine derivatives are chosen from 2,4,5,6-tetraminopyrimidine, 4-hydroxy-2,5,6-triaminopyrimidine, pyrazolopyrimidine derivatives, and acid addition salts of said pyrimidine derivatives.

10. The composition according to claim 9, wherein said pyrazolpyrimidine derivatives are chosen from pyrazolo pyrimidine-3,7-diamine, 2-methylpyrazolo pyrimidine-3,7-diamine, 2,5-dimethylpyrazolo pyrimidine-3,7-diamine, pyrazolo pyrimidine-3,5-diamine, 2,7-dimethylpyrazolo pyrimidine-3,5-diamine, 3-aminopyrazolo pyrimidin-7-ol, 3-amino-5-methylpyrazolo pyrimidin-7-ol, 3-amino-pyrazolo pyrimidin-5-ol, 2-(3-aminopyrazolo-pyrimidin-7-ylamino)ethanol, 3-amino-7-α-hydroxyethylamino-5-methylpyrazolo pyrimidine, 2-(7-aminopyrazolo pyrimidin-3-ylamino)ethanol, 2-ethanol, 2-ethanol, 5,6-dimethylpyrazolo pyrimidine-3,7-diamine, 2,6-dimethylpyrazolo pyrimidine-3,7-diamine, and 2,5,N7,N7-tetramethylpyrazolo pyrimidine-3,7-diamine, and acid addition salts of said pyrazolpyrimidine derivatives and tautomeric forms of said pyrazolpyrimidine derivatives, when a tautomeric equilibrium exists.

11. The composition according to claim 8, wherein said pyrazole derivatives are chosen from 4,5-diaminopyrazole, 4,5-diamino-1-methyl-pyrazole, 1-benzyl-4,5-diaminopyrazole, 3,4-diamino-pyrazole, 1-benzyl-4,5-diamino-3-methylpyrazole, 4-amino-1,3-dimethyl-5-hydrazinopyrazole, 4,5-diamino-3-methyl-1-phenylpyrazole, 4,5-diamino-1-tert-butyl-3-methylpyrazole, 4,5-diamino-3-tert-butyl-1-methyl-pyrazole, 4,5-diamino-1-ethyl-3-methylpyrazole, 4,5-diamino-1-ethyl-3-(4i-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, and acid addition salts of said pyrazole derivatives.

12. The composition according to claim 1, wherein said heterocyclic couplers are chosen from benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo-oxazoline derivatives, pyrazolo-thiazole derivatives, thiazoloazole S-oxide derivatives, thiazoloazole S,S-dioxide derivatives, and acid addition salts of said heterocyclic couplers.

13. The composition according to claim 12, wherein said benzimidazole derivatives are chosen from the compounds of formula (I), and their acid addition salts:

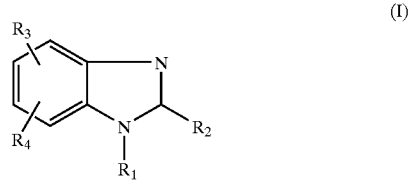

(I)

in which:
R$_1$ is chosen from hydrogen and C$_1$–C$_4$ alkyl groups,
R$_2$ is chosen from hydrogen, C$_1$–C$_4$ alkyl groups, and phenyl groups,
R$_3$ is chosen from hydroxyl groups, amino groups, and methoxy groups,
R$_4$ is chosen from hydrogen, hydroxyl groups, methoxy groups, and C$_1$–C$_4$ alkyl groups;
with the proviso that:
(a) when R$_3$ is an amino group, then it occupies position 4;
(b) when R$_3$ occupies position 4, then R$_4$ occupies position 7; and
(c) when R$_3$ occupies position 5, then R$_4$ occupies position 6.

14. The composition according to claim 12, wherein said benzimidazole derivatives are chosen from 4-hydroxybenzimidazole, 4-amino-benzimidazole, 4-hydroxy-7-methylbenzimidazole, 4-hydroxy-2-methylbenzimidazole, 1-butyl-4-hydroxy-benzimidazole, 4-amino-2-methylbenzimidazole, 5,6-dihydroxybenzimidazole, 5-hydroxy-6-methoxy-benzimidazole, 4,7-dihydroxybenzimidazole, 4,7-dihydroxy-1-methylbenzimidazole, 4,7-dimethoxy-benzimidazole, 5,6-dihydroxy-1-methylbenzimidazole, 5,6-dihydroxy-2-methylbenzimidazole, 5,6-dimethoxy-benzimidazole, and acid addition salts of said benzimidazole derivatives.

15. The composition according to claim 12, wherein said benzimidazole derivatives are chosen from compounds of formula (II), and their acid addition salts:

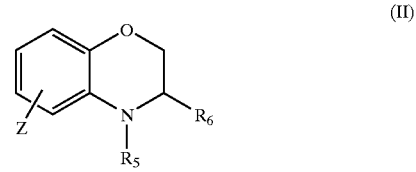

(II)

in which:
R$_5$ and R$_6$, which may be identical or different, are each chosen from hydrogen and C$_1$–C$_4$ alkyl groups; and
Z is chosen from hydroxyl groups and amino groups.

16. The composition according to claim 12, wherein said benzomorpholine derivatives are chosen from 6-hydroxy-1,4-benzomorpholine, N-methyl-6-hydroxy-1,4-benzomorpholine, 6-amino-1,4-benzomorpholine, and acid addition salts of said benzomorpholine derivatives.

17. The composition according to claim 12, wherein said sesamol derivatives are chosen from the compounds of formula (III) and their acid addition salts:

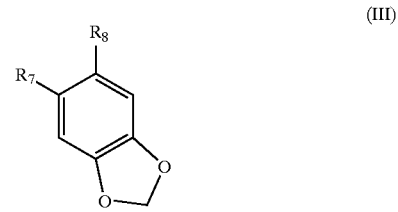

(III)

in which:
R$_7$ is chosen from hydroxyl groups, amino groups, (C$_1$–C$_4$)alkylamino groups, monohydroxy (C$_1$–C$_4$) alkylamino groups, and polyhydroxy(C$_2$–C$_4$)alkyl-amino groups;
R$_8$ is chosen from hydrogen, halogens, and (C$_1$–C$_4$) alkoxy groups.

18. The composition according to claim 17, wherein said sesamol derivatives of formula III are chosen from 2-bromo-4,5-methylenedioxyphenol, 2-methoxy-4,5-methylene-dioxyaniline and 2-(β-hydroxy-ethyl)amino-4,5-methylene-dioxybenzene, and acid addition salts of said sesamol derivatives.

19. The composition according to claim 12, wherein said pyrazoloazole derivatives are chosen from:
2-methylpyrazolo-1,2,4-triazole,
2-ethylpyrazolo-1,2,4-triazole,
2-isopropylpyrazolo-1,2,4-triazole,
2-phenylpyrazolo-1,2,4-triazole,
2,6-dimethylpyrazolo-1,2,4-triazole,
7-chloro-2,6-dimethylpyrazolo-1,2,4-triazole, 3,6-dimethylpyrazolo-1,2,4-triazole,
6-phenyl-3-methylthiopyrazolo-1,2,4-triazole,
6-aminopyrazolo benzimidazole,
and acid addition salts of said pyrazoloazole derivatives.

20. The composition according to claim 12, wherein said pyrroloazole derivatives are chosen from:
5-cyano-4-ethoxycarbonyl-8-methylpyrrolo-1,2,4-triazole,
5-cyano-8-methyl-4-phenylpyrrolo-1,2,4-triazole,
7-amido-6-ethoxycarbonylpyrrolo benzimidazole,
and acid addition salts of said pyrroloazole derivatives.

21. The composition according to claim 12, wherein said imidazoloazole derivatives are chosen from:
7,8-dicyanoimidazolo imidazole,
7,8-dicyano-4-methylimidazolo imidazole,
and acid addition salts of said imidazoloazole derivatives.

22. The composition according to claim 12, wherein said pyrazolopyrimidine derivatives are chosen from:
pyrazolo pyrimidin-7-one,
2,5-dimethylpyrazolo pyrimidin-7-one,
2-methyl-6-ethoxycarbonylpyrazolo pyrimidin-7-one,
2-methyl-5-methoxymethylpyrazolo pyrimidin-7-one,
2-tert-butyl-5-trifluoromethylpyrazolo pyrimidin-7-one,
2,7-dimethylpyrazolo pyrimidin-5-one,
and acid addition salts of said pyrazolopyrimidine derivatives.

23. The composition according to claim 12, wherein said pyrazoline-3,5-dione derivatives are chosen from:
1,2-diphenylpyrazoline-3,5-dione,
1,2-diethylpyrazoline-3,5-dione,
and acid-addition salts of said-pyrazoline-3,5-dione derivatives.

24. The composition according to claim 1, wherein said at least one oxidation dye is present in a concentration ranging from about 0.0001% to about 12% by weight relative to the total weight of said composition.

25. The composition according to claim 1, wherein said at least one oxidation dye is present in a concentration ranging from about 0.005% to about 6% by weight of the total weight of said composition.

26. The composition according to claim 1, further comprising:
(a) at least one benzenic oxidation base chosen from para-phenylenediamines, bis(phenylalkylenediamines, orthophenylenediamines, para-aminophenols, ortho-aminophenols, and acid addition salts of said benzenic oxidation base,
(b) at least one benzenic coupler chosen from meta-phenylenediamines, meta-aminophenols, meta-diphenols and acid addition salts of said benzenic coupler, and
(c) at least one direct dye.

27. The composition according to claim 1, wherein said acid addition salts of said at least one oxidation dye are chosen from hydrochlorides, hydrobromides, sulphates, tartrates, lactates, and acetates.

28. The composition according to claim 1, further comprising at least one carrier which is suitable for dyeing keratin fibers.

29. The composition according to claim 28, wherein said at least one carrier is chosen from water and at least one organic solvent.

30. The composition according to claim 1, wherein said composition has a pH ranging from about 4 to about 11.

31. A method of dyeing keratinous fibers, comprising the step of applying at least one dyeing composition to said keratinous fibers for a sufficient time to achieve a desired coloration, wherein said at least one dyeing composition comprises:

(a) at least one oxidation base chosen from heterocyclic oxidation bases, heterocyclic couplers, and acid addition salts of said oxidation dyes, provided that said dyeing composition does not comprise a heterocyclic oxidation base chosen from 4,5-diamino-6-hydroxy-pyrimidine and 3,4-diaminohydroxypyrazole; and provided that said dyeing composition does not comprise a heterocyclic coupler chosen from indole, indoline, monocyclic pyridine, and phenazine compounds; and
(b) at least one enzyme of the laccase type.

32. A method for dyeing keratinous fibers comprising the steps of:
(a) storing a first composition;
(b) storing a second composition separately from said first composition;
(c) mixing said first composition with said second composition to form a mixture; and
(d) applying said mixture to said keratinous fibers for a sufficient time to achieve a desired coloration;
wherein said first composition comprises at least one oxidation base chosen from heterocyclic oxidation bases, heterocyclic couplers, and acid addition salts of said oxidation dyes, in a medium appropriate for dyeing keratinous fibers, provided that said first composition does not comprises a heterocyclic oxidation base chosen from 4,5-diamino-6-hydroxy-pyrimidine and 3,4-diaminohydroxypyrazole; and provided that said first composition does not comprise a heterocyclic coupler chosen from indole, indoline, monocyclic pyridine, and phenazine compounds; and
wherein said second composition comprises at least one enzyme of the laccase type, in a medium appropriate for dyeing keratinous fibers.

33. A multicompartment device or a dyeing kit, comprising:
a first compartment containing a first composition comprising at least one oxidation base chosen from heterocyclic oxidation bases, heterocyclic couplers, and acid addition salts of said oxidation dyes, provided that said composition does not comprise a heterocyclic oxidation base chosen from 4,5-diamino-6-hydroxy-pyrimidine and 3,4-diaminohydroxypyrazole; and provided that said composition does not comprise a heterocyclic coupler chosen from indole, indoline, monocyclic pyridine, and phenazine compounds, in a medium appropriate for dyeing keratinous fibers; and
a second compartment containing a second composition comprising at least one enzyme of the laccase type, in a medium appropriate for dyeing keratinous fibers.

34. The composition according to claim 1, wherein said at least one enzyme of the laccase type is chosen from laccases of fungal origin.

35. The composition according to claim 34, wherein said laccases of fungal origin are obtained by biotechnology.

36. The composition according to claim 1, wherein said at least one enzyme of the laccase type is chosen from laccases of plant origin, laccases of animal origin, and laccases of bacterial origin.

37. The composition according to claim 1, wherein said at least one enzyme of the laccase type is chosen from laccases obtained by biotechnology.

* * * * *

UNITED STATES PATENT AND TRADEMARK OFFICE
CERTIFICATE OF CORRECTION

PATENT NO. : 6,893,470 B1
DATED : May 17, 2005
INVENTOR(S) : Gérard Lang et al.

It is certified that error appears in the above-identified patent and that said Letters Patent is hereby corrected as shown below:

Column 10,
Line 61, "tetraminopyrimidine" should read -- tetraaminopyrimidine --.
Line 67, "2,5-dimethylpyrazolo" should read -- 2,5-dimethyl pyrazolo --.

Column 11,
Lines 5-6, "3-amino-7-α-hydroxyethylamino-5-methylpyrazolo" should read
-- 3-amino-7-β-hydroxyethylamino-5-methylpyrazolo --.

Column 13,
Line 29, "said-pyrazoline-3,5-dione" should read -- said pyrazoline-3,5-dione --.

Column 14,
Line 27, "does not comprises" should read -- does not comprise --.

Signed and Sealed this

Sixteenth Day of August, 2005

JON W. DUDAS
*Director of the United States Patent and Trademark Office*